United States Patent
Wang et al.

(10) Patent No.: US 12,044,574 B2
(45) Date of Patent: Jul. 23, 2024

(54) NON-CONTACT BODY TEMPERATURE MEASUREMENT DEVICE

(71) Applicant: NATIONAL SUN YAT-SEN UNIVERSITY, Kaohsiung (TW)

(72) Inventors: Fu-Kang Wang, Kaohsiung (TW); Pin-Hsun Juan, Kaohsiung (TW); Ya-Chi Su, Kaohsiung (TW); Yu-Chieh Wang, Kaohsiung (TW); Ju-Yin Shih, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 253 days.

(21) Appl. No.: 17/875,614

(22) Filed: Jul. 28, 2022

(65) Prior Publication Data
US 2023/0304865 A1     Sep. 28, 2023

(30) Foreign Application Priority Data
Mar. 24, 2022 (TW) ................... 111111214

(51) Int. Cl.
*G01J 5/00*     (2022.01)
*A61B 5/01*     (2006.01)

(52) U.S. Cl.
CPC .............. *G01J 5/0025* (2013.01); *A61B 5/01* (2013.01); *G01J 5/0066* (2013.01); *G01J 2005/0077* (2013.01)

(58) Field of Classification Search
CPC ...... G01J 5/0025; G01J 5/0066; G01J 5/0022; G01J 2005/0077; A01K 29/005; A01K 29/00; G01T 1/00; A61B 5/015; A61B 5/01; A61B 2562/0271
See application file for complete search history.

(56) References Cited

FOREIGN PATENT DOCUMENTS

| CN | 108955900 A | 12/2018 |
|---|---|---|
| CN | 112595420 A | 4/2021 |
| CN | 113218507 A | 8/2021 |
| CN | 113313866 A | 8/2021 |
| KR | 101837026 B1 * | 3/2018 |
| TW | 202143908 A | 12/2021 |

OTHER PUBLICATIONS

Fu-Kang Wang et al., Non-Invasive Cattle Body Temperature Measurement Using Infrared Thermography and Auxiliary Sensors, MDPI Sensors, Apr. 1, 2021.
Taiwanese Office Action mailed Jun. 9, 2023 for Taiwanese Patent Application No. 111111214, 7 pages.

\* cited by examiner

*Primary Examiner* — Don K Wong
(74) *Attorney, Agent, or Firm* — Demian K. Jackson; Jackson IPG PLLC

(57) ABSTRACT

A non-contact body temperature measurement device includes a thermal imager, an anemometer and a processing unit. The thermal imager is provided to capture thermal images. The anemometer is provided to measure wind speed and output a wind speed signal. The processing unit is provided to process the thermal images according to the wind speed signal and remove the thermal image showing great variation in temperature between two consecutive frames. Consequently, an accurate body temperature can be measured through the processed thermal images.

11 Claims, 4 Drawing Sheets

NON-CONTACT BODY TEMPERATURE MEASUREMENT DEVICE

FIELD OF THE INVENTION

This invention generally relates to a body temperature measurement device, and more particularly to a non-contact body temperature measurement device.

BACKGROUND OF THE INVENTION

Body temperature is one of important indicators of livestock healthy. A rise in body temperature may affect milk production and fertility, and partial rise or fall in body temperature may be related to lesion position. Hence, body temperature measurement and monitoring are quite important in livestock agriculture. Rectal temperature measurement using contact-type thermometer is a common way to measure livestock core temperature, but it is labor-intensive and livestock may feel uncomfortable and nervous during measurement. Body temperature variation level is responsive to change of cattle diseases, such as heat stress and bovine mastitis. However, long-term monitoring of cattle body temperature using contact-type thermometer is impracticable to assess disease state. Non-contact monitoring is required for livestock body temperature measurement.

SUMMARY

The object of the present invention is to process thermal images captured by a thermal imager according to wind speed measured using an anemometer and remove the thermal image(s) showing significant temperature difference between two consecutive frames. Thus, the effects caused by environmental factors and subject's body movement can be minimized to improve accuracy of non-contact boy temperature measurement.

A non-contact body temperature measurement device of the present invention includes a thermal imager, an anemometer and a processing unit. The thermal imager is used to capture thermal images each including pixels. The anemometer is used to measure wind speed and output a wind speed signal. The processing unit is electrically connected to the thermal imager and the anemometer to receive the thermal images and the wind speed signal. The processing unit is provided to determine whether to remove one of the thermal images based on the wind speed signal to obtain first thermal images, provided to designate the region in the each of the first thermal images where the pixel showing the highest temperature as a region of interest, and provided to determine whether a temperature difference of the region of interest between two consecutive frames of each of the first thermal images is higher than a temperature difference threshold. If the temperature difference is higher than the temperature difference threshold, the processing unit is provided to remove the later frame of the first thermal image and output second thermal images.

In the present invention, the thermal images captured by the thermal imager are processed based on the wind speed signal and temperature variation level. The thermal image(s) affected by air flow and the thermal image(s) showing a significant temperature difference between two consecutive frames are removed to eliminate the influence of air flow and the subject's body movement. Thus, the results measured from the processed thermal images by a way of non-contact body temperature measurement are improved to close to real body temperature of the subject.

DETAILED DESCRIPTION OF THE INVENTION

Figure 1:
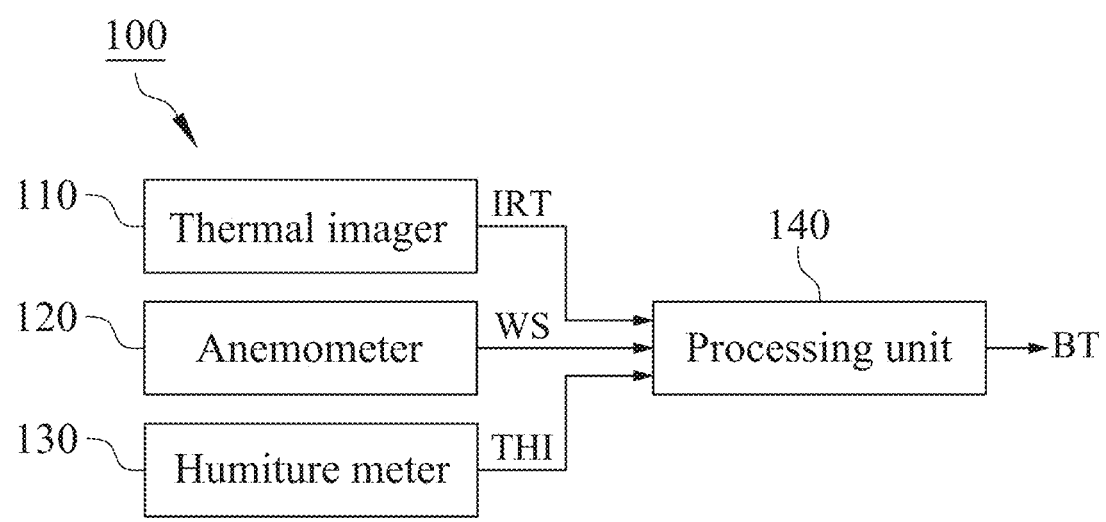
FIG. 1 is a block diagram illustrating a non-contact body temperature measurement device in accordance with one embodiment of the present invention.

With reference to FIG. 1, a non-contact body temperature measurement device 100 in accordance with one embodiment of the present invention includes a thermal imager 110, an anemometer 120, a humiture meter 130 and a processing unit 140.

The thermal imager 110 is an infrared thermal imager and used to capture infrared images and output thermal images IRT, and there is a subject in each of the thermal images IRT. The thermal images IRT are discrete-time data of frames and each includes pixels showing temperature data. Thus, the thermal images IRT can be applied for measuring the subject's body temperature.

As the non-contact body temperature measurement device 100 of the present invention is provided to measure body temperature of a livestock, the thermal imager 110 is placed toward the livestock face to capture thermal images IRT of eye socket of the livestock owing to it is difficult to measure body temperature from livestock skin with fur. The measured temperature of eye socket of the livestock is close to the core temperature of the livestock. The region of interest is not limited to the eye socket of the livestock in the present invention, the thermal imager 110 can be used to capture thermal images of other region on the livestock for other purpose, such as lesion location.

The thermal images IRT captured with the thermal imager 110 are used to measure surface temperature of the subject, but the surface temperature is easily affected by air flow to be reduced. Consequently, the anemometer 120 is provided to detect wind speed and output a wind speed signal WS in this embodiment, the wind speed signal WS is used to process the thermal images IRT.

Furthermore, the subject may be moving to reduce the surface temperature during the thermal imager 110 captures the thermal images IRT. In this embodiment, temperature difference between two consecutive frames of the thermal images IRT are used to determine whether the subject is moving so as to prevent the thermal images IRT from being affected by body movement of the subject.

In order to eliminate the effect caused by wind speed during body temperature measurement, the processing unit 140 is used to determine whether to remove one of the thermal images IRT to obtain a plurality of first thermal images based on the wind speed signal WS in this embodiment. The thermal image(s) IRT captured by the thermal imager 100 under a wind speed is not 0 is/are removed by the processing unit 140, and the unremoved thermal images IRT are output as the first thermal images. After surface temperature of the subject is affected by wind speed, the surface temperature needs response time to recovery, preferably, the recovery time is set to a margin of 1 to 3 frames. Accordingly, 1 to 3 frames of the thermal image(s) IRT after a point of time when the wind speed is not 0 is/are removed by the processing unit 140 to fully deduct the thermal image(s) IRT affected by wind speed, and the other thermal images IRT are output as the first thermal images.

Figure 2A:
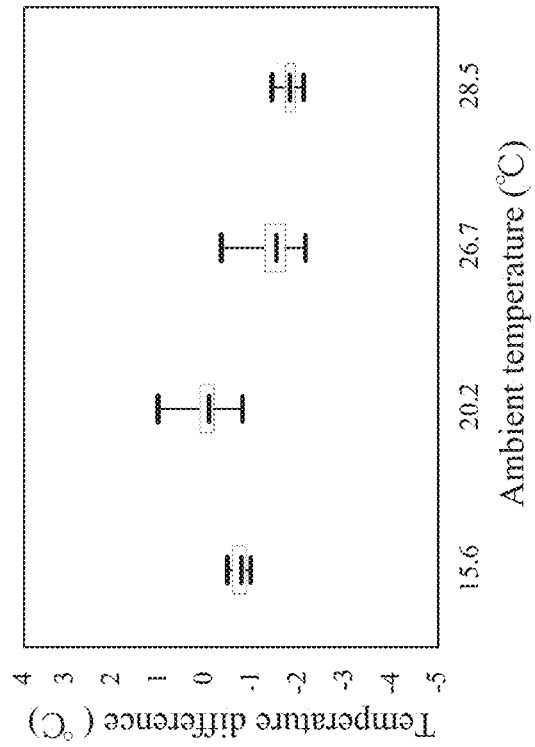
FIG. 2*a* is a box plot diagram showing difference between surface temperature obtained from thermal image captured by thermal imager and rectal temperature measured using contact-type thermometer under different ambient temperature before eliminating the effect caused by wind.
Figure 2B:
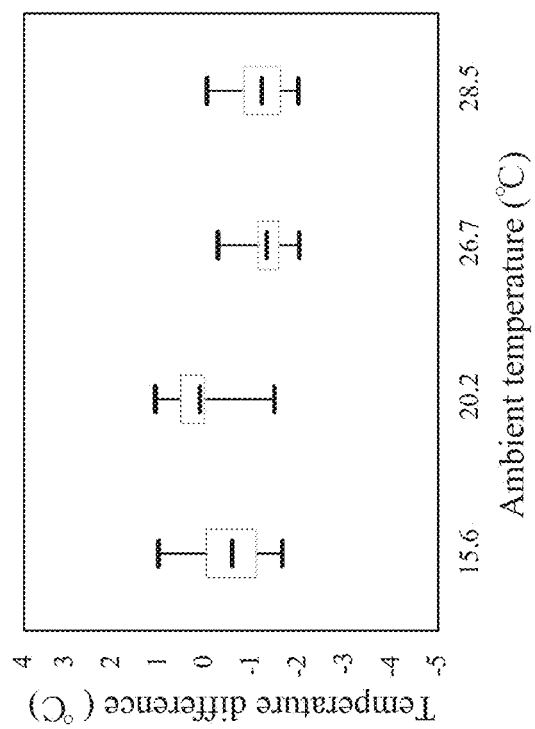
FIG. 2*b* is a box plot diagram showing difference between surface temperature obtained from thermal image captured by thermal imager and rectal temperature measured using contact-type thermometer under different ambient temperature after eliminating the effect caused by wind.

FIG. 2a is a box plot diagram showing difference between cow's surface temperature obtained from the thermal image IRT captured by the thermal imager 110 and cow's rectal temperature measured using contact-type thermometer under different ambient temperature, temperature errors are obvious under different ambient temperature before eliminating the effect caused by wind speed. As shown in FIG. 2b which is a box plot diagram showing temperature error after eliminating the effect caused by wind speed, temperature errors are reduced significantly. The result proves that the effect of wind speed is actually eliminated to reduce temperature error using the device 100 of this embodiment of the present invention.

Not only wind speed, random body movement of the subject also affects body temperature measurement. In this embodiment, the processing unit 140 designates the region in each of the first thermal images where is the pixel showing the highest temperature (the highest temperature spot) as a region of interest, and determines whether temperature difference of the region of interest between two consecutive frames of each of the first thermal images is greater than a temperature difference threshold. If the temperature difference is greater than the temperature difference threshold, it represents that the movement of the subject occurs within the two consecutive frames, and the processing unit 140 needs to remove the later frame of each of the first thermal images to obtain a plurality of second thermal images. In this embodiment, the temperature difference threshold is plus or minus 1° C.

After removing the thermal images affected by air flow and body movement of the subject, the error between the surface temperature acquired through the second thermal images and the body temperature measured using a contact-type thermometer is reduced to acceptable range. The processing unit 140 can calculate a mean value of the highest temperatures in the second thermal images and output the mean value as a body temperature BT. Consequently, non-contact body temperature measurement is available using the device 100 of the present invention.

As there are two or more pixels showing high temperature in the thermal image IRT captured by the thermal imager 110, there may be not only one subject captured in the thermal image IRT and this may generate a false result of body temperature measurement, so the thermal image IRT is required to be deleted. However, if there are two high-temperature spots, such as eyes of livestock, showing in the thermal image IRT of a single subject, the thermal image IRT can be retained.

Preferably, the region where is the pixel showing a temperature higher than a temperature threshold in each of the thermal images IRT is designated as a high-temperature region by the processing unit 140. While there are two or more high-temperature regions found in each of the thermal images IRT, the processing unit 140 needs to estimate whether the distance between the high-temperature regions is less than or equal to a distance threshold. If the distance between the high-temperature regions is not greater than the distance threshold, the two high-temperature regions may be the subject's eyes or two different parts of the eye socket of the subject, and the thermal image IRT can be retained. In contrast, if the distance between the high-temperature regions is greater than the distance threshold, the two high-temperature regions may be resulted from two different subjects, and the thermal image IRT has to be removed. The distance between two high-temperature regions can be given by $$\sqrt{(i_k-i_m)^2+(j_k-j_m)^2} \leq d$$

where $(i_k, j_k)$ and $(i_m, j_m)$ are the pixel coordinate locations of the two high-temperature regions, respectively, and d is the distance threshold. In this embodiment, the temperature threshold is set between 36 and 40° C. based on different subjects and purposes, and the distance threshold is set between 14 and 18 pixels according to the distance between the thermal imager 110 and the subject.

For example, the thermal imager 110 is installed to target eye socket of cow for non-contact body temperature measurement, the temperature threshold can be set as 37 or 38° C. owing to the normal body temperature of cow is about 38.6° C., the distance threshold can be set as 15 or 16 pixels because the distance of cow's eyes on the thermal image IRT is about 16 pixels while the thermal imager 110 is placed one meter away from the cow. According to the temperature threshold and the distance threshold mentioned above, the device 100 of the present invention can remove the thermal image(s) IRT capturing more than one subjects and save the thermal image(s) IRT showing two high-temperature spots of the same subject.

Environmental temperature and humidity may influence accuracy of temperature readings on the thermal images IRT, for this reason, a temperature-humidity index THI generated by the humiture meter 130 is used to calibrate the mean value calculated by the processing unit 140 in this embodiment. Preferably, the humiture meter 130 senses an environmental temperature and a relative humidity, and then generates the temperature-humidity index THI based on the environmental temperature and the relative humidity. The temperature-humidity index THI is shown in the following equation:

$$THI=(1.8 \times T_e+32)-(0.55-0.005 \times H_e) \times (1.8 \times T_e-26)$$

where THI is the temperature-humidity index, $T_e$ is the environmental temperature, and $H_e$ is the relative humidity. The subject's body temperature is measured using the thermal imager 110 under different temperature-humidity index in advance to acquire temperature differences between the measured temperatures and rectal temperatures measured using contact-type thermometer, the temperature differences are provided to generate a temperature difference-environmental temperature curve by curve fitting, and the temperature difference-environmental temperature curve is symmetric about the X axis (X=0, in other words, the temperature difference=0) to acquire a correction function of the temperature-humidity index THI. In calibration of temperature and humidity, the processing unit 140 substitutes the temperature-humidity index THI sensed by the humiture meter 130 at present to the correction function of the temperature-humidity index THI to calculate a temperature error value, and output a calibrated value which is the mean value added with the temperature error value as the body temperature BT.

Figure 3B:
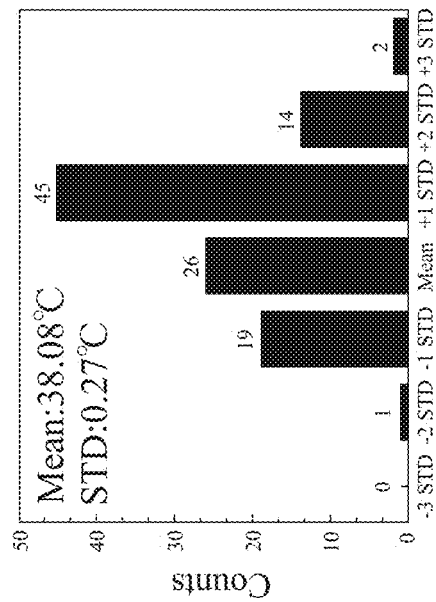
FIG. 3*b* is a histogram of data distribution of original body temperature of 107 measured by a thermal imager.
Figure 3A:
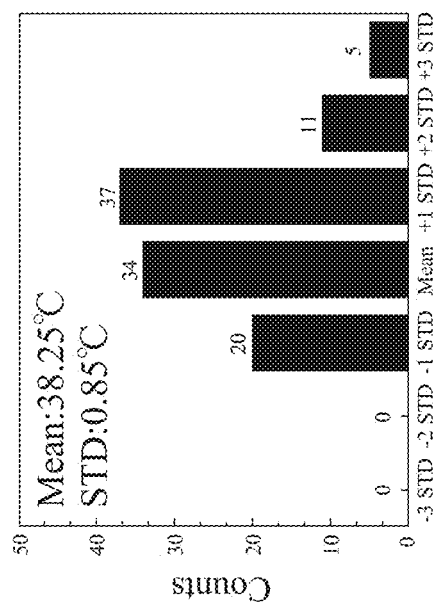
FIG. 3*a* is a histogram of data distribution of rectal temperature of 107 entries using a contact-type thermometer.
Figure 3C:
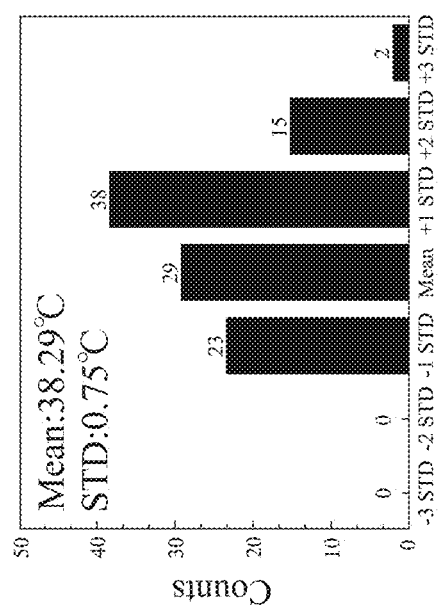
FIG. 3*c* is a histogram of data distribution of body temperature of 107 entries measured by a non-contact body temperature measurement device in accordance with one embodiment of the present invention.

FIG. 3a is a histogram of data distribution of rectal temperature measured using a rectal thermometer, FIG. 3b is a histogram of data distribution of original surface temperature measured using the thermal imager 110, and FIG. 3c is a histogram of data distribution of processed surface temperature using the non-contact body temperature measurement device 100 in accordance with one embodiment of the present invention. Mean and STD shown in the diagrams represent mean value and standard deviation value, respectively. The readings processed by the device 100 of the present invention is closer to the rectal temperature measured by contact-type thermometer than the original readings measured by the thermal imager 110. Data processing by this embodiment of the present invention actually can improve the influence of environmental factors on the thermal images.

In the present invention, the thermal images IRT captured by the thermal imager 110 are processed according to the wind speed signal WS. The thermal image(s) IRT affected by air flow and the thermal image(s) IRT showing great variation in temperature between two consecutive frames resulted from body movement of the subject are removed, thus, temperature readings measured by the processed thermal images IRT is quite close to real body temperature of the subject. Non-contact body temperature measurement with high accuracy is practical using the architecture of the present invention.

The scope of the present invention is only limited by the following claims. Any alternation and modification without departing from the scope and spirit of the present invention will become apparent to those skilled in the art.

What is claimed is:

1. A non-contact body temperature measurement device comprising:
    a thermal imager configured to capture a plurality of thermal images, each of the plurality of thermal images includes a plurality of pixels;
    an anemometer configured to detect wind speed and output a wind speed signal; and
    a processing unit electrically connected to the thermal imager and the anemometer to receive the plurality of thermal images and the wind speed signal, wherein the processing unit is configured to determine whether to remove one of the plurality of thermal images according to the wind speed signal and obtain a plurality of first thermal images, and the processing unit is configured to designate the region in each of the plurality of first thermal images where is the pixel showing the highest temperature as a region of interest and configured to determine whether a temperature difference of the region of interest between two consecutive frames of each of the plurality of first thermal image is higher than a temperature difference threshold, and the processing unit is configured to remove the later frame of each of the plurality of first thermal images and obtain a plurality of second thermal images while the temperature difference of the region of interest is higher than the temperature difference threshold.

2. The non-contact body temperature measurement device in accordance with claim 1, wherein the processing unit is configured to remove one of the plurality of thermal images which is captured by the thermal imager at a point of time when the wind speed signal is not zero, and the processing unit is configured to output others of the plurality of thermal images as the plurality of first thermal images.

3. The non-contact body temperature measurement device in accordance with claim 1, wherein the processing unit is configured to remove one to three frames of the thermal image after a point of time when the wind speed signal is not zero, and the processing unit is configured to output others of the plurality of thermal images as the plurality of first thermal images.

4. The non-contact body temperature measurement device in accordance with claim 1, wherein the processing unit is configured to calculate a mean value of highest temperatures in the plurality of second thermal images and output the mean value as a body temperature.

5. The non-contact body temperature measurement device in accordance with claim 4 further comprising a humiture meter configured to measure a temperature-humidity index, wherein the processing unit is configured to calibrate the mean value with the temperature-humidity index and a correction function of the temperature-humidity index and output the calibrated mean value as the body temperature.

6. The non-contact body temperature measurement device in accordance with claim 5, wherein the processing unit is configured to substitute the temperature-humidity index to the correction function of the temperature-humidity index to calculate a temperature error value, and the processing unit is configured to output a calibrated value which is the mean value added with the temperature error value as the body temperature.

7. The non-contact body temperature measurement device in accordance with claim 5, wherein the humiture meter is configured to measure an environmental temperature and a relative humidity and configured to calculate the temperature-humidity index according to the environmental temperature and the relative humidity.

8. The non-contact body temperature measurement device in accordance with claim 7, wherein the processing unit is configured to substitute the temperature-humidity index to the correction function of the temperature-humidity index to calculate a temperature error value, and the processing unit is configured to output a calibrated value which is the mean value added with the temperature error value as the body temperature.

9. The non-contact body temperature measurement device in accordance with claim 1, wherein the processing unit is configured to designate the region in each of the plurality of first thermal images where is at least one of the plurality of pixels showing a temperature higher than a temperature threshold as a high-temperature region, wherein while there are two or more high-temperature regions designated in one of the plurality of first thermal images, the processing unit is configured to estimate whether a distance between the high-temperature regions is less than or equal to a distance threshold, and wherein while the distance is estimated to be greater than the distance threshold, the processing unit is configured to remove the first thermal image.

10. The non-contact body temperature measurement device in accordance with claim 9, wherein the temperature threshold is between 36 and 40° C., and the distance threshold is between 14 and 18 pixels.

11. The non-contact body temperature measurement device in accordance with claim 1, wherein the temperature difference threshold is plus or minus 1° C.

* * * * *